United States Patent [19]
DeHaven-Hudkins et al.

[11] Patent Number: 5,434,159
[45] Date of Patent: Jul. 18, 1995

[54] 6,11-CYCLYL-1,2,3,4,5,6,11,11A-OCTAHYDROBENZO[B]QUINOLINES AND COMPOSITIONS AND METHOD OF USE THEREOF

[75] Inventors: Diane L. DeHaven-Hudkins, West Pikeland Township, Chester County; William G. Earley, Lower Providence Township, Montgomery County; John P. Mallamo, Uwchlan Township, Chester County, all of Pa.; Garry M. Pilling, Nassau, N.Y.

[73] Assignee: Sterling Winthrop Inc., Malvern, Pa.

[21] Appl. No.: 320,013

[22] Filed: Oct. 7, 1994

Related U.S. Application Data

[63] Continuation of Ser. No. 121,121, Sep. 14, 1993, abandoned.

[51] Int. Cl.$^6$ .................. A61K 31/435; C07D 471/00
[52] U.S. Cl. ........................................ 514/281; 546/43
[58] Field of Search ........................... 544/43; 514/281

[56] References Cited

U.S. PATENT DOCUMENTS 3,517,073  6/1970  Fields .................................. 568/735

OTHER PUBLICATIONS

Fields, et al., J Org. Chem. 1968, 33(1), 390–395.
Fields and Regan, J. Org. Chem. 1971, 36(20), 2986–2990.
Fields and Regan, J. Org. Chem. 1971, 36(20), 2991–2994.
Fields, J. Org. Chem. 1971, 36(20), 3002–3005.
Westerman and Bradsher, J. Org. Chem. 1971, 36(7), 969–970.
Bradsher and Day, J. Het. Chem. 1973, 10, 1031–1033.
Fields and Regan, J. Org. Chem. 1970, 35(6), 1870–1875.
Fields et al., J. Org. Chem. 1971, 36(20), 2995–3001.
Fields and Miller, J. Het Chem. 1970, 7, 91–97.
Bradsher and Stone, J. Org. Chem. 1968, 33(2), 519–523.
Bradsher and Solomons, J. Am. Chem. Soc. 1958, 80, 933–934.
Bradsher and Stone, J. Org. Chem. 1969, 34(6), 1700–1702.
Burnham and Bradsher, J. Org. Chem. 1972, 37(3), 355–358.
Parham et al., J. Org. Chem. 1972, 37(3), 358–362.
Bradsher et al., J. Am. chem. Soc. 1977, 99(8), 2588–2591.
Bradsher et al., J. Org. Chem. 1978, 43(5), 822–827.
Westerman and Bradsher, J. Org. Chem. 1978, 43(15), 3002–3006.
Westerman and Bradsher, J. Org. Chem. 1979, 44(5), 727–733.
Bradsher et al., J. Org. Chem. 1979, 44(8), 1199–1201.
Hart et al., Tetrahedron Letters 1975, 52, 4639–4642.

*Primary Examiner*—Mukund J. Shah
*Assistant Examiner*—Matthew V. Grumbling
*Attorney, Agent, or Firm*—Michael D. Alexander; Paul E. Dupont

[57] ABSTRACT

6,11′-Cyclyl-1,2,3,4,5,6,11,11a-octahydrobenzo[b]quinolizine derivatives, pharmaceutical compositions containing them and methods for the treatment or prevention of neurodegenerative disorders or neurotoxic injuries utilizing them.

24 Claims, No Drawings

6,11-CYCLYL-1,2,3,4,5,6,11,11A-OCTAHYDROBEN-ZO[B]QUINOLINES AND COMPOSITIONS AND METHOD OF USE THEREOF

CROSS REFERENCE TO RELATED APPLICATIONS

This application is a continuation of our prior application Ser. No. 08/121,121, filed Sep. 14, 1993 now abandoned.

BACKGROUND OF THE INVENTION a) Field of the Invention

The invention relates to 6,11-cyclyl-1,2,3,4,5,6,11,11a-octahydrobenzo[b]quinolizines, to compositions containing the same, and to the method of use thereof in the treatment or prevention of neurodegenerative disorders or neurotoxic injuries.

b) Information Disclosure Statement

Fields, U.S. Pat. No. 3,517,073 issued Jun. 23, 1970, discloses compounds of the formula:

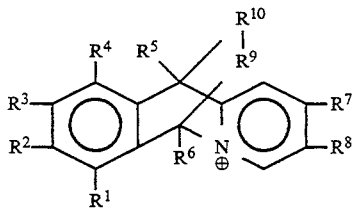

wherein each of $R^1$, $R^2$ $R^3$ and $R^4$ when taken separately, is hydrogen, lower alkyl, lower aryl, lower acyloxy, lower alkoxy, nitro, halogen, lower acylamino, all(lower alkyl) amino; one group of $R^1$ and $R^2$, $R^2$ and $R^3$, and $R^3$ and $R^4$, preferably $R^1$ and $R^2$, and $R^3$ and $R^4$, each group when taken together, represents a fused ring system containing up to three 6-member carbocyclic and nitrogen-containing heterocyclic rings at least one of which is an aromatic ring, and having no more than two nuclear nitrogens in any ring, which may be unsubstituted or substituted with one or more of the substituents defined by $R^1$, $R^2$, $R^3$ and $R_4$; each of $R^5$ and $R^6$, when taken separately is hydrogen, lower alkyl or lower aryl; each of $R^7$ and $R^8$, when taken separately, is hydrogen; $R^7$ and $R^8$, when taken together, represent a fused ring system as defined hereinbefore; $R^9$, when taken individually, is methylene or lower alkyl, lower aryl, lower alkenyl, halogen, or cyano substituted methylene; $R^{10}$, when taken individually, is a protected carbonyl group; $R^9$ and $R^{10}$, when taken together, represent a fused aromatic carbocyclic or heterocyclic ring system, whose valence bonds are from adjacent carbons, containing up to three 6-membered carbocyclic and nitrogen-containing heterocyclic rings having no more than two nitrogens in any ring and which may be substituted with one or more of the substituents defined by $R^1$, $R^2$, $R^3$ and $R^4$. Among the compounds specifically disclosed are 12,12-diethoxy-11-methyl-9,10-ethano-9,10-dihydro-4a-azoniaanthracene perchlorate and 9,10-(O-benzeno)-9,10-dihydro-5-methyl-4a-azoniaanthracene perchlorate. Also disclosed are compounds of the formula:

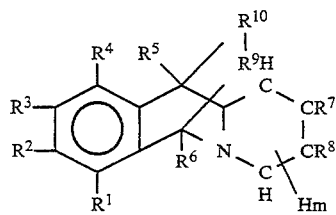

wherein $R^1$–$R^{10}$ are as defined above and m is an odd integer having a value of from 1 to 5, inclusive. Among the compounds specifically disclosed are 12,12-diethoxy-11-methyl-9,10-ethano-4a-aza-1,2,3,4,4a, 9,9a,10-octahydroanthracene perchlorate acid salt, 9, 10-(O-benzeno) -5-methyl-4a-aza-1,2,3,4,4a,9,9a,10-octahydroanthracene and 12,12-diethoxy-9,10-ethano-11-bromo-4a-aza-1,2,3,4,4a,9,9a,10-octahydroanthracene. The above-described compounds are disclosed as being intermediates in the synthesis of 2-napthol derivatives and various anthracene derivatives.

Fields et al., J. Org. Chem. 1968, 33(1), 390–395, disclose a series of sixteen Dieis-Alder adducts prepared from a 4a-azoniaanthracene ion and various dienophiles. Among the compounds specifically disclosed are 12-ethyl, 12-hydroxymethyl and 12-ethylene-9,10-dihydro-4a-azonia-9,10-ethanoanthracene bromides; 12-phenyl-12-(4-morpholinyl), 12-methyl-12-(1-methylethylene), 12,12-diethoxy-11-bromo and 12-diethylamino-11-phenyl-9,10-dihydro-4a-azonia-9,10-ethanoanthracene perchlorates, as well as 9,10 [1',2']cyclopentyl and 9,10 [2', 3']tetrahydropyranyl-9,10-dihydro-4a-azoniaanthracene perchlorates. No utility is disclosed for these compounds.

Fields and Regan, J. Org. Chem. 1971, 36(20), 2986–2990, disclose compounds of the formula:

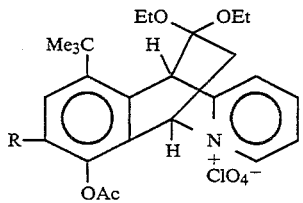

wherein R is H, Br, or OAc, as intermediates in the synthesis of substituted 8-tert-butyl-1-(2-pyridyl) napthalenes.

Fields and Regan, J, Org. Chem. 1971, 36(20), 2991–2994, disclose compounds of the formula:

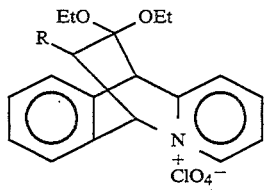

wherein R is H, $CH_3$, $C_6H_5$, or Br, as intermediates in the synthesis of 2-pyridylnapthols.

Fields, J. Org. Chem. 1971, 36(20), 3002–3005, discloses a series of substituted 12,12-diethoxy-9,10-ethano-9,10-dihydro -4a-azoniaanthracenes and the corresponding derivatives wherein the pyridinium moiety is partially or completely reduced, as intermediates in the synthesis of substituted 2-napthols. Among the compounds specifically disclosed is 12,12-diethoxy-5,11-dimethyl-9,10-ethano-9,10-dihydro-4a-azoniaanthracene perchlorate. Also disclosed is a series of substituted 9,10-(O-benzeno)-9,10-dihydro-4a-azoniaanthracenes and the corresponding derivatives wherein the pyridinium moiety is partially or completely reduced, as intermediates in the synthesis of substituted anthracenes. Among the compounds specifically disclosed is 9,10-(O-benzeno)-9,10-dihydro-4a-azoniaanthracene perchlorate.

Westerman and Bradsher, J. Org. Chem. 1971, 36(7), 969-970, disclose compounds of the formula:

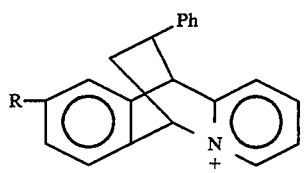

wherein R is $CH_3$, $CH(CH_3)_2$, H, F, I, Cl, Br, $CO_2H$, $CO_2CH_3$, or $NO_2$. No utility is disclosed for these compounds.

Bradsher and Day, J. Her. Chem. 1973, 10, 1031-1033, disclose four Dieis-Alder adducts prepared from acridizinium perchlorate and cyclopentadiene, methyl vinyl ether, norbornadiene and maleic anhydride. No utility is disclosed for these compounds.

Fields and Regan, J. Org. Chem. 1970, 35(6), 1870-1875, disclose compounds of the formula:

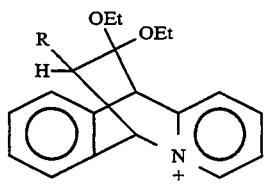

wherein R is H, $CH_3$ or $C_6H_5$. Also specifically disclosed are 9,10-dihydro-12,12-dimethoxy-11, 11-dimethyl-4a-azonia-9,10-ethanoanthracene perchlorate and 9,10-dihydro-9,11-dimethyl-12,12-diethoxy-4a-azonia-9,10-ethanoanthracene perchlorate. The compounds are said to be intermediates in the synthesis of 9,10-dihydro-12-oxo-4a-azonia-9,10-ethanoanthracenes.

Fields et al., J. Org. Chem. 1971, 36(20), 2995-3001, disclose 9,10-dihydro-4a-azonia-9,10-O-benzenoanthracene perchlorate and several analogs as intermediates in the synthesis of various 9-(2-pyridyl)anthracenes.

Fields and Miller, J. Her. Chem. 1970, 7, 91-97, disclose a compound of the formula:

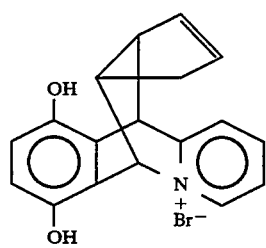

as an intermediate in the synthesis of the corresponding 5,8-dione salt.

Bradsher and Stone, J. Org. Chem. 1968, 33(2), 519-523, disclose a series of Dieis-Alder adducts prepared from an acridizinium ion and maleic anhydride, maleate esters, fumarate esters and various para-substituted styrenes in which the para substituent is H, $CH_3$, $OCH_3$ or $NO_2$. No utility is disclosed for these compounds. A substantially similar disclosure for the preparation of Dieis-Alder adducts from acridizinium bromide and maleic anhydride, maleate or fumarate esters can be found in Bradsher and Solomons, J. Am. Chem. Soc. 1958, 80, 933-934.

Bradsher and Stone, J. Org. Chem. 1969, 34(6), 1700-1702, disclose compounds of the formula:

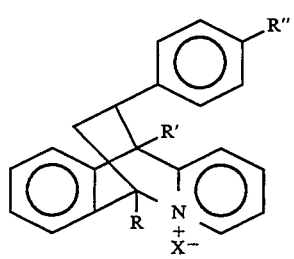

wherein R is H, or $CH_3$; R' is H, or $CH_3$; R" is $OCH_3$, $CH_3$, H, or $NO_2$; and $X^-$ is perchlorate; without an indication of utility. Also disclosed are the Dieis-Alder adducts obtained from acridizinium perchlorate and diethyl maleate, diethyl fumarate or dimethyl maleate, without an indication of utility.

Burnham and Bradsher, J. Org. Chem. 1972, 37(3), 355-358, disclose compounds of the formula:

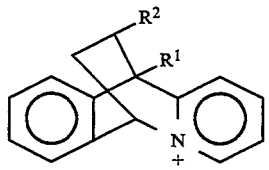

wherein $R^1$ is Ph, and $R^2$ is OEt; or $R^1$ is H, and $R^2$ is OEt, OBu, OAc, N-carbazolyl or 1-pyrrolidin-2-one, without an indication of utility.

Parham et al., J. Org. Chem. 1972, 37(3), 358-362, disclose compounds of the formula:

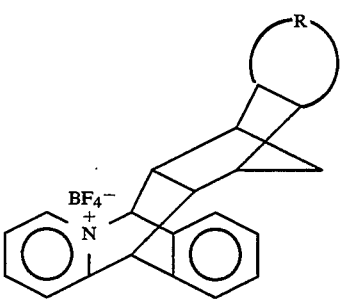

wherein R is $H_2$, $(CH_2)_3$, C(O)NHC(O), $C(O)N(CH_3)$-C(O), C(O)OC(O), $CH_2OCH_2$, or $CH_2NH_2^+CH_2$, without an indication of utility.

Bradsher et al., J. Am. Chem. Soc. 1977, 99(8), 2588-2591, disclose compounds of the formula:

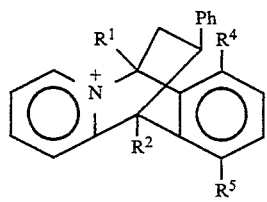

wherein: $R^1=R^2=R^4=R^5=H$; $R^1=Me$, and $R^2=R^4=R^5=H$; $R^1=R^4=R^5=H$, and $R^2=Me$; and $R^1=H$ and $R^2=R^4=R^5=Me$. No utility is disclosed for these compounds.

Bradsher et al., J. Org. Chem. 1978, 43(5), 822–827, disclose compounds of the formula:

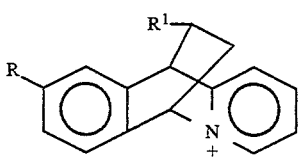

wherein: $R^1$ is OEt and R is Me, H, F, Cl, $CO_2Me$ or $NO_2$; $R^1$ is O -Ph-p-X, wherein X is $CH_3$, $OCH_3$, H, C(O) $CH_3$, or $NO_2$, and R is hydrogen; and $R^1$ is N-carbazolyl and R is hydrogen. No utility is disclosed for these compounds.

Westerman and Bradsher, J. Org. Chem. 1978, 43(15), 3002–3006, disclose a series of Dieis-Alder adducts prepared from an acridizinium ion and various unsymmetrical alkenes, without an indication of utility. Among the compounds specifically disclosed are 6,11 [2′,3′]indanyl-6,11-dihydroacridizinium tetrafluoroborate, and 12-phenyl-13-(2-pyridyl)-6,11-dihydro-6,11-ethanoacridizinium tetrafluoroborate.

Westerman and Bradsher, J. Org. Chem. 1979, 44(5), 727–733, disclose a series of Dieis-Alder adducts prepared from a substituted or unsubstituted acridizinium cation and various polarizable alkenes without an indication of utility. Among the compounds specifically disclosed are 12,12-diphenyl-6,11-dihydro-6,11-ethanoacridizinium perchlorate or bromide, 9-methyl-6,11 [2′3′]indanyl-6,11-dihydroacridizinium tetrafluoroborate, and 7,10-dimethyl-12-phenyl-12-(4-morpholinyl), 9-methyl-12-phenyl-12-(4-morpholinyl), 12-(2-pyridyl), and 9-methyl-12-(2-pyridyl)-6,11-dihydro-6,11-ethanoacridizinium tetrafluoroborates.

Bradsher et al., J. Org. Chem. 1979, 44(8), 1199–1201, disclose a series of Dieis-Alder adducts prepared from a substituted or unsubstituted acridizinium ion and cyclopropene or 1-methylcyclopropene, without an indication of utility.

Hart et al., Tetrahedron Letters 1975, 52, 4639–4642, disclose a compound of the formula:

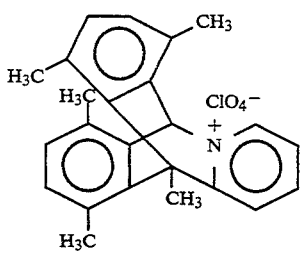

as an intermediate in the synthesis of 1,4,5,8,9-pentamethylanthracene.

SUMMARY OF THE INVENTION

The invention relates to compounds of the Formula I:

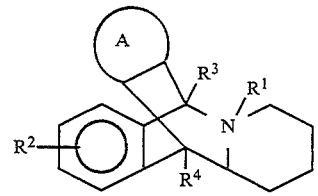

I wherein:
$R^1$ is lower-alkyl, $O^-$, or a free valence;
$R^2$ is hydrogen, or one substituent in any of the 7-, 8-, 9-, or 10-positions selected from the group consisting of amino, halogen, hydroxy, and lower-alkoxy;
$R^3$ is hydrogen, or lower-alkyl;
$R^4$ is hydrogen, or lower-alkyl; and
A is a cycloalkyl ring, or a saturated monocyclic 5-or 6-membered heterocyclic ring containing a single oxygen heteroatom;
or a pharmaceutically acceptable acid-addition salt of basic members thereof; or when $R^1$ is lower-alkyl a quaternary ammonium salt thereof.

The compounds of the Formula I bind to the PCP receptor and are thus useful in the treatment or prevention of neurodegenerative disorders or neurotoxic injuries.

Preferred compounds of the Formula I above are those wherein $R^2$ is hydrogen, or one substituent in any of the 8-, 9-, or 10-positions selected from the group consisting of amino, halogen and hydroxy; A is a cycloalkyl, [2′,3′]tetrahydrofuranyl, or [2′,3′]tetrahydropyranyl; and $R^1$, $R^3$ and $R^4$ are as defined above.

Particularly preferred compounds of the Formula I above are those wherein:
$R^1$ is methyl, $O^-$, or a free valence;
$R^2$ is hydrogen, or one substituent in any of the 8-, 9-, or 10-positions selected from the group consisting of amine, bromine, fluorine and hydroxy;
$R^3$ is hydrogen or methyl;
$R^4$ is hydrogen or methyl; and
A is a cycloalkyl, [2′,3′]tetrahydrofuranyl, or 2′,3′]tetrahydropyranyl ring.

The invention further relates to pharmaceutical compositions which comprise a compound of the Formula I:

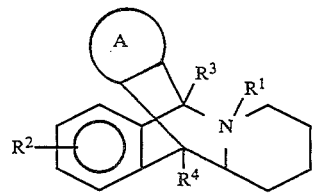

I wherein:
$R^1$ is lower-alkyl, $O^-$, or a free valence;
$R^2$ is hydrogen, or one substituent in any of the 7-, 8-, 9-, or 10-positions selected from the group consisting of amino, halogen, hydroxy, and lower-alkoxy;

R³ is hydrogen, or lower-alkyl;

R⁴ is hydrogen, or lower-alkyl;

A is a cycloalkyl ring, a phenyl ring, or a saturated monocyclic 5-or 6-membered heterocyclic ring containing a single oxygen heteroatom; or a pharmaceutically acceptable acid-addition salt of basic members thereof; or when R¹ is lower-alkyl a quaternary ammonium salt thereof; together with a pharmaceutically acceptable carrier, adjuvant, diluent, or vehicle.

The invention further relates to a method for the treatment or prevention of neurodegenerative disorders, or neurotoxic injuries which comprises administering to a patient in need of such treatment an effective amount of a compound of the Formula I:

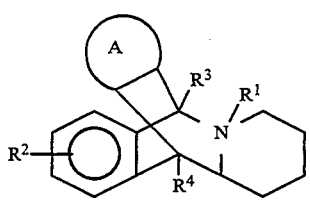

I wherein:

R¹ is lower-alkyl, O⁻, or a free valence;

R² is hydrogen, or one substituent in any of the 7-, 8-, 9-, or 10-positions selected from the group consisting of amino, halogen, hydroxy, and lower-alkoxy;

R³ is hydrogen, or lower-alkyl;

R⁴ is hydrogen, or lower-alkyl;

A is a cycloalkyl ring, a phenyl ring, or a saturated monocyclic 5-or 6-membered heterocyclic ring containing a single oxygen heteroatom; or a pharmaceutically acceptable acid-addition salt of basic members thereof; or when R¹ is lower-alkyl a quaternary ammonium salt thereof.

DETAILED DESCRIPTION INCLUSIVE OF PREFERRED EMBODIMENTS

The term lower-alkyl as used herein means linear or branched hydrocarbon chains having one to about four carbon atoms and thus includes methyl, ethyl, isopropyl, n-butyl, sec-butyl, and the like.

The term lower-alkoxy as used herein means linear or branched alkyloxy substituents having one to about four carbon atoms and thus includes methoxy, ethoxy, propoxy, isopropoxy, butoxy, sec-butoxy, and the like.

The term halogen or halide as used herein means bromine, chlorine, iodine, and fluorine.

The term cycloalkyl as used herein means C₅ through C₇ saturated monocyclic hydrocarbon residues and thus includes cyclopentyl, cyclohexyl and cycloheptyl.

The term cycloalkenyl as used herein means C₅ through C₇ unsaturated monocyclic hydrocarbon residues and thus includes cyclopentenyl, cyclohexenyl and cycloheptenyl.

The term anion (X⁻) as used herein means the anion of an organic acid (includes anions of organic monoacids, as well as monoanions of organic diacids) which is at least as strong as acetic acid, and thus includes anions of such acids as acetic acid, methanesulfonic acid, toluenesulfonic acid, trifluoromethanesulfonic acid, (−)-dibenzoyl-L-tartaric acid [(−)-DBT], (+)dibenzoyl-D-tartaric acid [(+)-DBT], and the like; or it means an inorganic acid anion such as chloride, bromide, perchlorate, PF₆⁻ and the like, preferably chloride.

The numbering system used throughout the specification is shown in the ring system which is illustrated below. It should

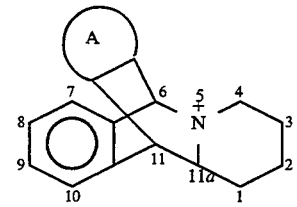

be noted, however, that in some of the earlier chemical literature references (see references cited in Information Disclosure Statement) this ring system, wherein A is a phenyl ring, was numbered as shown below, and was named as a 9,10-(benzeno) -4a-aza-1,2,3,4,4a,9,9a,10-octahydroanthracene. Throughout this specification however, we will use the former numbering system and accordingly, the compounds of the invention will be named as 6,11-cyclyl (e.g. cycloalkyl, heterocyclyl and benzeno)-1,2,3,4,5,6,11,11a-octahydrobenzo[b]quinolizines.

The synthesis of the compounds of the invention may be outlined as shown in Scheme A:

Scheme A

II

I

-continued
Scheme A

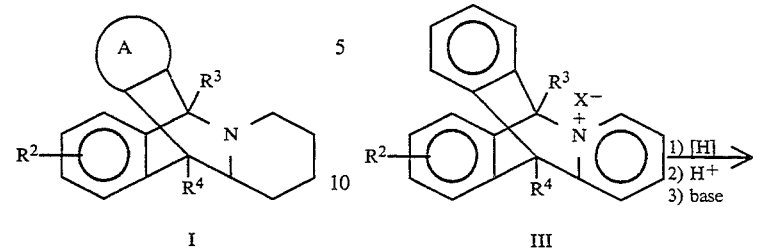

I

A suitably substituted 6,11-cyclyl-6,11-dihydrobenzo[b-]quinolizinium salt of Formula II, wherein X⁻ is an anion and A is a cycloalkyl, cycloalkenyl, phenyl, or a saturated monocyclic 5- or 6-membered heterocyclic ring containing a single oxygen heteroatom, is hydrogenated on a Parr hydrogenator, in the presence of a catalyst, preferably platinum oxide, in a suitable organic solvent, e.g. tetrahydrofuran, methanol, ethanol, or a mixture thereof, optionally in the presence of an excess of an aqueous acid (HX), preferably 6N HCl, to produce the compounds of the Formula I, wherein $R^1$ is a free valence, as the HX⁻ salts. If desired, these salts can be treated with an excess of an appropriate base, e.g. concentrated NH₄OH, 6N KOH, saturated NaHCO₃, 35% NaOH, 1N NaOH or 10% K₂CO₃, to produce the compounds of the Formula I as the free base. The bases thus generated can then be interacted with the same acid (HX) or a different acid to produce the same or different acid-addition salt. It should be noted that in compounds of the Formula II, wherein A is a phenyl ring or a cycloalkenyl ring, the phenyl ring and the cycloalkenyl ring are also reduced under the above described reaction conditions to produce the compounds of the Formula I wherein A is a cyclohexyl ring, or a cycloalkyl ring, respectively.

In those instances when a compound of the Formula I wherein A is phenyl is desired, it is convenient to proceed as shown in Scheme B:

Scheme B

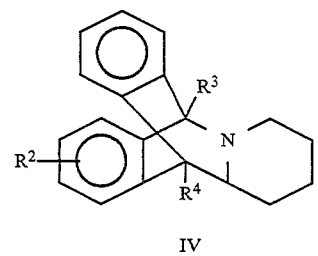

III

IV

A suitably substituted 6,11-benzeno-6,11-dihydrobenzo[b]quinolizinium salt of Formula III (Formula II wherein A is phenyl) is treated with an excess of a reducing agent, preferably sodium borohydride, in an alcoholic solvent, e.g. methanol, at a temperature of about room temperature, followed by acidification with a suitable acid, e.g. 2N HCl, and then basification with a suitable base, e.g. concentrated NH₄OH, to produce a compound of the Formula IV (Formula I wherein A is phenyl).

In those instances wherein a compound of the Formula I wherein $R^2$ is amino is desired, it is convenient to hydrogenate a compound of the Formula II, wherein $R^2$ is nitro, as described hereinabove in Scheme A to produce the corresponding compounds of the Formula I wherein the $R^2$=nitro group has been reduced to the corresponding $R^2$=amino group.

In those instances wherein a compound of the Formula I, wherein $R^1$ is lower-akyl, or O⁻, is desired it is convenient to proceed as shown in Scheme C:

Scheme C

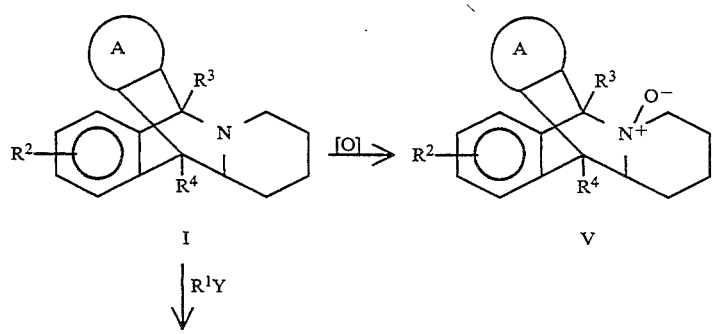

I      V

Scheme C

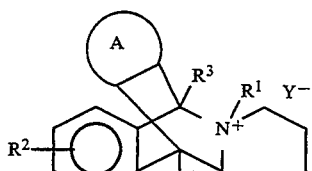

VI

A suitably substituted compound of the Formula I, wherein R¹ is a free valence, in an alcoholic solvent, e.g. methanol, can be treated with an excess of an oxidizing agent, e.g. 30% hydrogen peroxide, at a temperature in the range of about 0° C. up to about room temperature, to produce the compounds of the Formula V (Formula I wherein R¹=O⁻). The suitably substituted compound of the Formula I, wherein R¹ is a free valence, in an appropriate organic solvent, such as ethyl acetate, can also be treated with an excess of a compound of the formula R¹Y, wherein R¹ is lower-alkyl and Y is a suitable leaving group, preferably, bromine, chlorine, or iodine, at a temperature in the range of about 0° C. up to the boiling point of the solvent used, to produce the compounds of the Formula VI (Formula I wherein R¹ is lower-alkyl and Y⁻ represents the counter ion of the quaternary ammonium salt).

If a compound of the Formula I, wherein R² is hydroxy is desired, one can dealkylate a compound of the Formula I, wherein R² is lower-alkoxy, utilizing procedures which are conventional and well known to those skilled in the art of chemistry, for example, treating said compound of Formula I wherein R² is lower-alkoxy with an excess of an acid, such as 48% HBr, at a temperature in the range of about room temperature up to the boiling point of the acid.

It will be appreciated that the compounds of the Formula I can possess one or more asymmetric carbon atoms and are thus capable of existing in a number of stereoisomeric forms, e.g. enantiomers, diastereomers, and geometric isomers. Unless otherwise specified herein, the invention is intended to extend to each of these stereoisomeric forms, and to mixtures thereof, including the racemates. In some cases there may be advantages, e.g. greater potency, to using a particular enantiomer when compared to the other enantiomer or the racemate in the treatment or prevention of neurodegenerative disorders or neurotoxic injuries, and such advantages can be readily determined by those skilled in the act. The different stereoisomeric forms may be separated one from the other by conventional procedures which are well known in the art of chemistry, for example, diastereomers/geometric isomers can be separated by chromatography, fractional crystallization,and the like; and the resolution of enantiomers can be accomplished by fractional crystallization of their salts with optically active acids from appropriate solvents, chiral chromatography and the like.

The suitably substituted 6,11-cyclyl-6,11-dihydrobenzo[b]quinolizinium salts of Formula II, which are required for the synthesis of the compounds of the Formula I, can be prepared as shown in Scheme D.

Scheme D

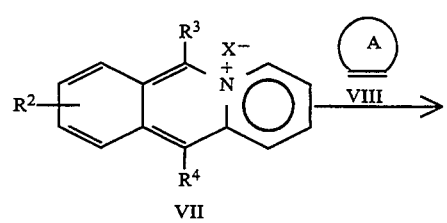

VII

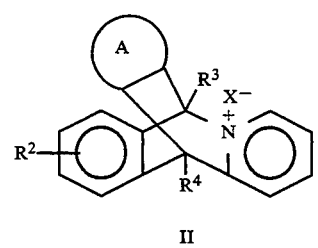

II

A suitably substituted benzo[b]quinolizinium salt of Formula VII can be treated with an excess of an appropriate cyclic diene or olefin of the Formula VIII, in a suitable organic solvent, e.g. acetonitrile, nitromethane, sulfolane, or alcoholic solvents such as methanol, or mixtures of said solvents, at a temperature in the range of about 0° C. up to the boiling point of the solvent or solvent mixture used to produce the compounds of the Formula II wherein A is a cycloalkyl, cycloalkenyl, or a saturated monocyclic 5-or 6-membered heterocyclic ring containing a single oxygen heteroatom. The corresponding compounds of the Formula II wherein A is a phenyl ring can be prepared by procedures which are known in the art of chemistry, for example, treating an appropriately substituted benzo[b]quinolizinium salt of Formula VII in a suitable solvent, e.g. acetonitrile, concurrently with an excess of isoamyl nitrite and anthranilic acid in the same solvent, followed by the addition of ether to precipitate the compound of the Formula II wherein A is phenyl (see, for example, Fields et al., J. Org. Chem. 1971, 36(20), 2995-3001).

If desired, the 6,11-cyclyl-6,11-dihydrobenzo[b-]quinolizinium salts of the Formula II can be converted into other compounds of the Formula II which possess various different anion groups, X⁻, by treating a solution of a compound of the Formula II in water with at least one molar equivalent of the alkali metal salt of an organic acid anion, or an inorganic acid anion, M⁺X⁻, wherein the acid of the salt used is a stronger acid than the corresponding acid of the initial acid anion (X⁻), and wherein M⁺ is an alkali metal, preferably potassium or sodium, at a temperature of about room temperature.

The suitably substituted benzo[b]quinolizinium salts of the Formula VII, which are required for the synthesis of the compounds of the Formula II, are either known and can thus be prepared by procedures which are known in the art of chemistry (see for example, Bradsher and Parham, J. Org. Chem., 1963, 28, 83-85; Bradsher and Jones, J. Am. Chem. Soc., 1957, 79, 6033-34; Bradsher et al., J. Her. Chem. 1964, 1, 30-33; and Bradsher and Parham, J. Her. Chem. 1964, 1, 121-124); or if they are novel, they can be prepared by the procedures described in the art or those described hereinbelow and illustrated in Schemes E and F. In Scheme E, at least one molar equivalent of an appropriately substituted benzyl halide (IX), wherein Z is a halogen, preferably chlorine, bromine, or iodine, is treated with one mole

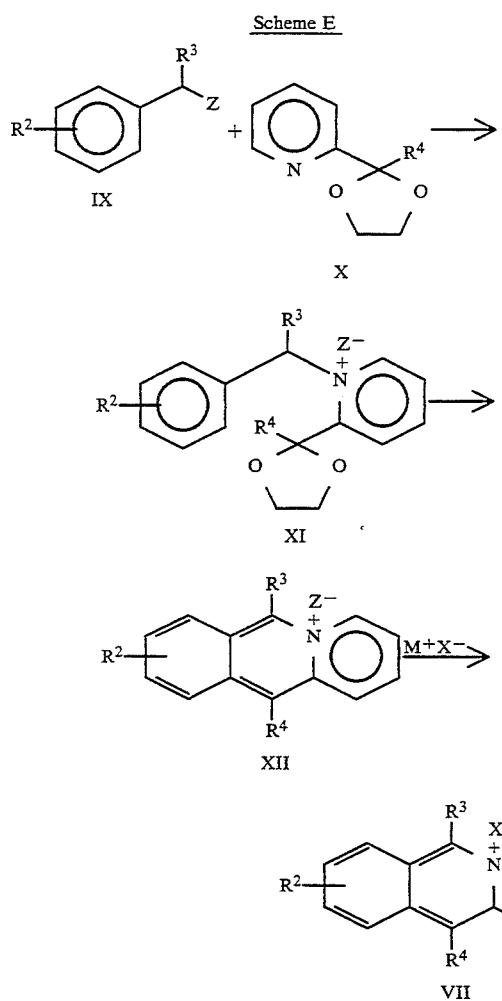

of an appropriately substituted 2-(1,3-dioxolan-2-yl)pyridine (X), in the presence of a solvent, e.g. sulfolane, or acetone, at a temperature in the range of about room temperature up to the boiling point of the solvent used, to produce the pyridinium salt (XI). The pyridinium salt (XI) can then be treated with an excess of an acid, e.g. polyphosphoric acid, 48% hydrobromic acid, or a mixture of polyphosphoric acid and methanesulfonic acid at a temperature in the range of about 40° C. up to the boiling point of the acid, or acid mixture used, to produce the compounds of the Formula XII (Formula VII wherein Z⁻=X⁻=halogen). The compounds of the Formula XII can then be converted into compounds of the Formula VII which possess various anion groups, X⁻, by (a) treating a compound of the Formula XII, either as a solution in water, or neat, with or adding it to an aqueous solution containing at least one molar equivalent of the alkali metal salt of an inorganic acid anion, M⁺X⁻, wherein the acid of the salt used is a stronger acid than the corresponding acid of the initial acid anion, and wherein M⁺ is an alkali metal, preferably potassium, lithium, or sodium, and X⁻ is as defined hereinabove; at a temperature in the range of about room temperature up to the boiling point of the aqueous solution, or (b) adding the alkali metal salt, M⁺X⁻, as a solid, to, or treating it with a solution of the compound of Formula XII in water, at a temperature in the range of about room temperature up to the boiling point of the aqueous solution.

Alternatively, the benzo[b]quinolizinium salts of Formula VII can be prepared as shown in Scheme F. A suitably substituted benzyl alcohol (XIII) is treated with at least two molar equivalents of a lower-alkyl alkali metal, preferably n-BuLi, optionally in the presence of at least one mole of a second base, e.g. tetramethylethylenediamine, followed by addition of an excess of a suitable pyridine derivative (XIV), in an organic solvent, such as ether, at room temperature or below, preferably at a temperature in the range of about room temperature to about

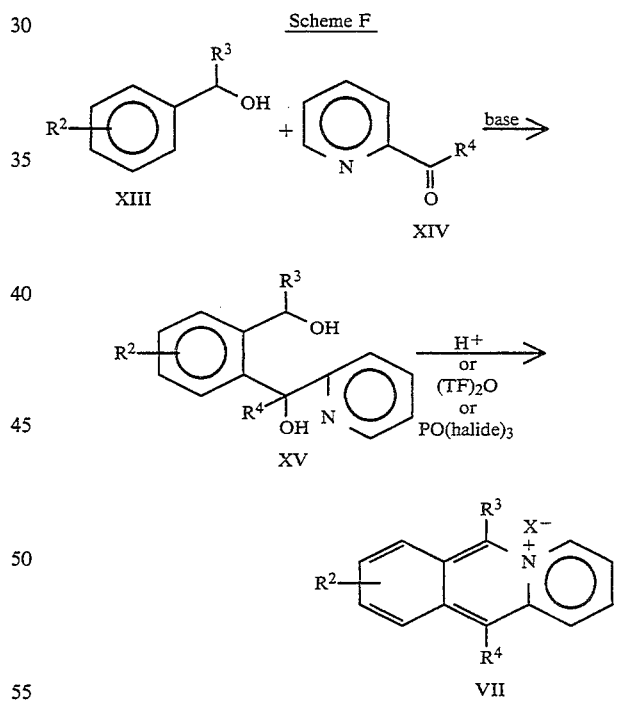

−30° C., to afford diol XV. The diol XV can then be treated with a) an excess of an acid, e.g. 45% hydrobromic acid in acetic acid, at a temperature in the range of room temperature up to the boiling point of the acid used, or b) an excess of trifluoromethanesulfonic anhydride ((TF)₂O), in a suitable solvent, at about room temperature or above, or c) at least one molar equivalent of a phosphorous oxyhalide, preferably phosphorous oxychloride, at about room temperature or above, to produce the compounds of the Formula VII, which can in turn be converted into other benzo[b]quinolizinium salts of the Formula VII which possess various different anion groups, $X^-$, by following the procedures described hereinabove. It will be noted that the method described hereinabove in Scheme F is the preferred method when it is desired to prepare compounds of the Formula VII which contain substituents in the 6-, 10-, and/or 11-positions.

The appropriately substituted cyclic diene or olefin (VIII), lower-alkyl halide ($R^1Y$), the alkali metal salts of an inorganic acid anion ($M^+X^-$), benzyl halide (IX), 2-(1,3-dioxolan-2-yl)pyridine (X), benzyl alcohol (XIII) and pyridine derivative (XIV) are commercially available, or they can be prepared by procedures well known in the art, or by the procedures described hereinbelow.

The compounds of Formula I are useful both in the free base form and in the form of acid-addition salts, and, both forms are within the purview of the invention. The acid-addition salts are often a more convenient form for use; and in practice, use of the salt form inherently amounts to use of the base form. The acids which can be used to prepare the acid-addition salts include preferably those which produce, when combined with the free base, pharmaceutically-acceptable salts, that is, salts whose anions are relatively innocuous to the animal organism in pharmaceutical doses of the salts, so that the beneficial properties inherent in the free base are not vitiated by side effects ascribable to the anions. In practicing the present invention it is convenient to use the free base form or the hydrochloride, fumarate, toluenesulfonate, methanesulfonate or maleate salts. However, other appropriate pharmaceutically acceptable salts within the scope of the invention are those derived from other mineral acids and organic acids. The acid-addition salts of the basic compounds are prepared by standard procedures well known in the art which include, but are not limited thereto, dissolving the free base in an aqueous alcohol solution containing the appropriate acid and isolating the salt by evaporating the solution, or by reacting the free base and an acid in an organic solvent, in which case the salt separates directly, or is precipitated with a second organic solvent, or can be obtained by concentration of the solution. Although medicinally acceptable salts of the basic compounds are preferred, all acid-addition salts are within the scope of the present invention. All acid-addition salts are useful as sources of the free base form even if the particular salt per se is desired only as an intermediate product, as, for example, when the salt is formed for purposes of purification or identification, or when it is used as an intermediate in preparing a medicinally acceptable salt by, for example, ion exchange procedures.

The compounds of Formula I wherein $R^1$ is lower-alkyl exist in the form of quaternary ammonium salts. The quaternary ammonium salts are prepared by standard procedures which are well known in the art, for example, alkylation of the free base with a suitable alkylating agent. The suitable alkylating agents which can be used to prepare the quaternary ammonium salts include preferably those which produce, when combined with the free base, pharmaceutically acceptable salts, that is, salts whose anions are relatively innocuous to the animal organism in pharmaceutical doses of the salts, so that the beneficial properties inherent in the compound are not vitiated by side effects ascribable to the anions. Representative examples of such anions include, but are not limited thereto, halides, methanesulfonates and toluenesulfonates.

The structures of the compounds of the invention were established by the mode of synthesis, and by one or more of elemental analysis, and infrared, nuclear magnetic resonance and mass spectroscopy. The course of the reactions and the identity and homogeneity of the products were assessed by one or more of thin layer chromatography (TLC), high pressure liquid chromatography (HPLC), or gas-liquid chromatography (GLC).

The following examples will further illustrate the invention without, however, limiting it thereto. All melting points (m.p.) are given in degrees centigrade (° C.) and are uncorrected. The abbreviation HCl stands for hydrochloric acid, NH$_4$OH stands for ammonium hydroxide, KOH stands for potassium hydroxide, NaHCO$_3$ stands for sodium bicarbonate, NaOH stands for sodium hydroxide, K$_2$CO$_3$ stands for potassium carbonate, n-BuLi stands for n-butyl lithium, HBr stands for hydrobromic acid, CH$_2$Cl$_2$ stands for dichloromethane, PtO$_2$ stands for platinium oxide, NaBH$_4$ stands for sodium borehydride, THF stands for tetrahydrofuran, and MgSO$_4$ stands for magnesium sulfate.

Preparation of Starting Materials

Preparation 1

To a mixture of benzo[b]quinolizinium bromide (10 g, 0.04 mol) (Bradsher and Parham, J. Org. Chem. 1963, 28, 83–85, Example VIIa) in 100 mL of acetonitrile/methanol (3:1) was added 3.55 g (0.044 mol) of 1,3-cyclohexadiene in 5 mL of acetonitrile/methanol (3:1) and the resulting solution was stirred at room temperature for 3 hours. The solvent was removed in vacuo and the residue was recrystallized from ethyl acetate/methylene chloride (3X) to afford 9.3 g (67%) of 6:11 [3′,4′]-cyclohexenyl -6,11-dihydrobenzo[b]quinolizinium bromide (Formula II: $R^2=R^3=R^4=H$; A=[3′,4′]-cyclohexenyl; $X^-=Br^-$), as an off-white solid, m.p. 285°–290° C.

Preparation 2

A solution containing 11-methyl-benzo[b]quinolizinium perchlorate (1.0 g, 3.4 mmol) (Bradsher and Parham, J. Org. Chem., 1963, 28, 83–85, Example VIII) and cyclopentadiene (2 mL, 23.4 mmol) in acetonitrile (40 mL) was stirred at room temperature for 2 hours. The solvent was removed in vacuo and the residue was triturated with ethyl acetate. The solid product was filtered to afford 1.2 g (97%) of 11-methyl-6,11-[3′,4′]cyclopentenyl-6,11-dihydrobenzo[b]quinolizinium perchlorate (Formula II: $R^2=R^3=H$; $R^1=CH_3$; A=[3′,4′]-cyclopentenyl; $X^-=ClO_4^-$).

Preparation 3

A solution of 8-methoxybenzo[b]quinolizinium perchlorate (3.2 g, 10.3 mmol) (Bradsher and Jones, J. Am. Chem. Soc, 1957, 79, 6033–34) in acetonitrile (100 mL) and methanol (35 mL) was cooled to 0° C. under nitrogen and cyclopentadiene (3.9 g, 59 mmol) was added. The mixture was stirred at room temperature overnight, followed by refluxing the reaction mixture for an additional 4 hours. The solvent was removed in vacuo and the residue was triturated with methanol, filtered, and the yellow solid thus obtained was washed with ether to afford 1.8 g (46%) of 8-methoxy-6,11 [3′,4′]cyclopentenyl-6,11-dihydrobenzo[b]quinolizinium perchlorate (Formula II: $R^2=8-OCH_3$; $R^3=R^4=H$; A=[3′,4′]-cyclopentenyl; $X^-=ClO_4^-$).

Preparation 4

(a)

A mixture of 2-(1,3-dioxolan-2-yl) pyridine (15.1 g, 0.1 mol) and 4-bromobenzyl-bromide (25.0 g, 0.1 mol) in tetramethylene sulfone (25 mL) was refluxed for 2 hours and allowed to stand for 16 hours. The reaction mixture was diluted with ethyl acetate (500 mL) and the solid product thus obtained was isolated by filtration to yield 37 g (92%) of 1-(4-bromobenzyl)-2-(1,3-dioxolan-2-yl)pyridinium bromide (Formula XI: $R^2=4-Br$; $R^3=R^4=H$; $Z^-=Br^-$) as a white solid.

(b)

A mixture of 1-(4-bromobenzyl)-2-(1,3-dioxolan-2-yl)-pyridinium bromide (37 g, 0.092 mol) in 48% HBr (300 mL) was refluxed with stirring for 24 hours. The reaction mixture was concentrated in vacuo and cold water (200 mL) was added to the residue. A yellow solid precipitated, which was isolated by filtration to yield 7.7 g (25%) of 9-bromobenzo[b]quinolizinium bromide (Formula VII: $R^2=9-Br$; $R^3=R^4=H$; $X^-=Br^-$).

(c)

To a mixture of 9-bromobenzo[b]quinolizinium bromide (7.7 g (0.0227 mol) in acetonitrile (75 mL) and nitromethane (75 mL) was added with stirring a solution of methanol (30 mL) and cyclopentadiene (10 mL). The mixture was stirred for 7 hours and allowed to stand for 16 hours. The solvent was removed in vacuo and the residue was triturated with acetonitrile and the solid product thus obtained was isolated by filtration. The product was recrystallized from ethanol to yield 7.2 g (78%) of 9-bromo-6,11 [3',4']cyclopentenyl-6,11-dihydrobenzo[b]quinolizinium bromide (Formula II: $R^2=9-Br$; $R^3=R^4=H$; $A=[3',4']$cyclopentenyl; $X^-=Br^-$), as a white solid, m.p. 277°–9° C. (dec).

Preparation 5

(a)

A mixture of 4-fluorobenzylbromide (17.5 g, 0.093 mol), sulfolane (25 mL) and 2-(1,3,-dioxolan-2-yl)pyridine (14.0 g, 0.093 mol) was stirred at room temperature for 2 hours, and then allowed to stand for 72 hours. The reaction mixture was diluted with ethyl acetate (200 mL) and the precipitate thus obtained was collected by filtration and washed with ether to afford 31.08 g (98%) of 1-(4-fluorobenzyl)-2-(1,3-dioxolan-2-yl)pyridinium bromide (Formula XI: $R^2=4-F$; $R^3=R^4=H$; $Z^-=Br^-$).

(b)

1-(4-Fluorobenzyl)-2-(1,3-dioxolan-2-yl)pyridinium bromide (31 g, 0. 091 mol) was added to a mixture of polyphosphoric acid (350 g) and methanesulfonic acid (100 mL) at 40° C. and the resulting mixture was heated at 105° C. for 2 hours. The mixture was poured onto ice and the solution was treated with charcoal. The mixture was added to an excess of sodium perchlorate and the solution was chilled and allowed to stand for 16 hours. A precipitate formed, which was collected by filtration to afford 15.9 g (59%) of 9-fluorobenzo[b]quinolizinium perchlorate (Formula VII: $R^2=9-F$; $R^3=R^4=H$; $X^-=ClO_4^-$), as a yellow solid, m.p. 168°–173° C.

(c)

To a mixture of 9-fluorobenzo[b]quinolizinium perchlorate (15.94 g, 0.0535 mol) in 100 mL of acetonitrile was added with stirring 18 g (0.27 mol) of cyclopentadiene. The reaction mixture was stirred at room temperature for 3 hours, then allowed to stand at room temperature for 16 hours. The solvent was removed in vacuo and the residue was triturated with ether. The ether was decanted, and the solid residue was stirred with ethyl acetate. The solid was collected by filtration and recrystallized from acetonitrile/ether to yield 14.73 g (75.5%) of 9-fluoro-6:11 [3',4']cyclopentenyl-6,11-dihydrobenzo-[b]quinolizinium perchlorate (Formula II: $R^2=9-F$; $R^3=R^4=H$; $A=[3',4']$cyclopentenyl; $X^-=ClO_4^-$), as a white solid, (m.p. 204°–5° C.).

Preparation 6

To a suspension of 9-nitrobenzo[b]quinolizinium perchlorate (2.6 g, 8 mmol) (Bradsher et al., J. Het. Chem. 1964, 1, 30–33) in acetonitrile (20 mL) was added cyclopentadiene (2.6 g, 0.039 mol) . The mixture was stirred until a homogeneous solution was obtained and the solution was filtered. The solvent was removed in vacuo and the residue thus obtained was recrystallized from acetonitrile to afford 1.3 g (42%) of 9-nitro-6:11 [3',4']cyclopentenyl-6,11-dihydrobenzo-[b]quinolizinium perchlorate (Formula II $R^2=9-F$; $R^3=R^4=H$; $A=[3',4']$cyclopentenyl; $X^-=ClO_4^-$), as a white powder, m.p. 235°–237° C. (dec.).

Preparation 7

A mixture of benzo [b]quinolizinium bromide (4.0 g, 15.4 mmol) (Bradsher and Parham, J. Org. Chem. 1963, 28, 83–85, Example VIIa), dihydropyran (40 mL) and tetramethylene sulfone (20 mL) was heated to reflux for 6 hours, and then stirred at room temperature overnight. The mixture was diluted with ethyl acetate (40 mL) and the precipitate thus obtained was collected by filtration to afford 3.5 g (66%) of 6,11 [2'3']tetrahydropyranyl -6,11-dihydrobenzo[b]quinolizinium bromide (Formula II: $R^2=R^3=R^4=H$; $A=[2',3']$tetrahydropyranyl; $X^-=Br^-$), as a white solid.

Preparation 8

A mixture of benzo[b]quinolizinium bromide (2.6 g, 10 mmol) (Bradsher and Parham, J. Org. Chem. 1963, 28, 83–85, Example VIIa), and 2,3-dihydrofuran (10 mL, 132 mmol) was heated to reflux and tetramethylene sulfone (10 mL) was added. The mixture was cooled to room temperature and stirred for 2 hours. The solvent was removed in vacuo, and the residue was stirred with ethyl acetate. A solid was collected by filtration and dried to afford 0.36 g (10%) of 6,11 [2',3']tetrahydrofuranyl-6,11-dihydrobenzo[b]quinolizinium bromide (Formula II: $R^2=R^3=R^4=H$; $A=[2',3']$tetrahydrofuranyl; $X^-=Br^-$), as a tan solid, m.p. 195°–200° C.

Preparation 9

To a solution of benzo[b]quinolizinium bromide (31 g, 0.12 mol) (Bradsher and Parham, J. Org. Chem. 1963, 28, 83–85, Example VIIa), in acetonitrile/methanol (3/1, 1000 mL) at room temperature was added in one portion freshly distilled cyclopentadiene (39.6 g, 0.6 mol). The mixture was stirred for 1.5 hours, and the solvent was removed in vacuo. The solid residue was slurried with ethyl acetate and the product was collected by filtration and the residue was recrystallized from methanol/tert-butylmethyl ether to afford 26.0 g (38%) of 6,11 [3',4']cyclopentenyl-6,11-dihydrobenzo[b]quinolizinium bromide (Formula II: $R^2=R^3=R^4=H$; $A=[3',4']$cyclopentenyl; $X^-=Br^-$).

Preparation 10

(a)

A mixture of 2-(1,3-dioxolan-2-yl)pyridine (19 g, 0.126 mol) and p-methoxybenzyl bromide (30 mL) in sulfolane (50 mL) was stirred at room temperature for 4.5 days. The reaction mixture was diluted with ethyl acetate and cooled while stirring. The solvent was decanted to isolate an opaque oil. The oil was triturated with ethyl acetate (3X) and a glassy solid was filtered to yield 15.72 g (40.6%) of 1-(4-methoxybenzyl-2-(1,3-dioxolan-2-yl)-pyridinium chloride (Formula XI: $R^2=4-OCH_3$; $R^3=R^4=H$; $Z^-=Cl^-$).

(b)

A mixture of 1-(4-methoxybenzyl)-2-(1,3-dioxolan-2-yl)pyridinium chloride (15 g, 0.049 mol) in 300 g of polyphosphoric acid was allowed to react at 120° C. for 3 hours. The reaction mixture was poured onto ice with stirring. The mixture was neutralized with dibasic sodium phosphate and an aqueous solution of lithium perchlorate (1.1 equiv.) was added. The precipitated solid was filtered and dried to yield 9-methoxybenzo[b]quinolizinium perchlorate (Formula VII: $R^2=OCH_3$; $R^3=R^4=H$; $X^-=ClO_4^-$), as a yellow solid.

(c)

A mixture of 13 g (0.042 mol) of 9-methoxybenzo[b]quinolizinium perchlorate and 30 mL (0.497 mol) of cyclopentadiene in 300 mL of methanol was stirred at room temperature for 24 hours. Additional cyclopentadiene (10 mL) was added and the reaction mixture was stirred for an additional 24 hours. The solvent was concentrated in vacuo and the dark residue was triturated with hexane and ethyl acetate respectively. The product was collected by filtration to afford crude 9-methoxy-6,11 [3',4']cyclopentenyl-6,11-dihydrobenzo[b]quinolizinium perchlorate (Formula II: $R^2=9=OCH_3$; $R^3=R^4=H$; $A=[3',4']$cyclopentenyl $X^-=ClO4^-$), which was used directly in subsequent transformations.

Preparation 11

(a)

To a solution of 3-methoxybenzylalcohol (50.0 g, 0.36 mol) in ether (1.1 L) at $-20°$ C. was added n-BuLi (76.0 mL, 0.756 mol) at such a rate that the internal temperature of the reaction was maintained at less than $-10°$ C. When the addition of n-BuLl was complete, the mixture was warmed to room temperature and stirred for 2 hours. The mixture was cooled to 0° C. and tetramethylethylene diamine (42.0 g, 0.36 reel) was added. The reaction mixture was cooled to $-30°$ C. and 2-pyridinecarboxaldehyde (58.0 g, 0.36 mol) was added over 5 minutes. The reaction was warmed to 0° C. over a 30 minute period and was then quenched with water (500 mL). The mixture was chilled for 24 hours, and the product was collected by filtration and washed with ether. The product was recrystallized from ethanol to afford 30.0 g (34%) of α-[2-(hydroxymethyl)-6-methoxyphenyl]-2-pyridinemethanol (Formula XV: $R^2=6-OCH_3$; $R^3=R^4=H$). The mother liquor from the recrystallization step was concentrated, diluted with ether and refrigerated for 16 hours. A solid precipitated, which was collected by filtration to afford an additional 13.1 g of the desired product for a total of 43.1 g (49%).

(b)

A solution of α-[2-(hydroxymethyl)-6-methoxyphenyl]-2-pyridinemethanol (13.1 g, 0.053 mol) in 45% hydrobromic acid in acetic acid (75 mL) was refluxed for 20 hours. Additional 45% hydrobromic acid in acetic acid (25 mL) was added and refluxing was continued for another 4 hours. The reaction mixture was cooled, poured into $CH_2Cl_2$ (700 mL) and stirred for several minutes. A solid precipitated, which was collected by filtration to afford 9.0 g (59%) of 10-methoxybenzo[b]quinolizinium bromide (Formula VII: $R^2=10-OCH_3$; $R^3=R^4=H$; $X^-=Br^-$). The filtrate was concentrated in vacuo to afford 4.0 g (27%) of 10-hydroxybenzo [b]quinolizinium bromide (Formula VII: $R^2=10=OH$; $R^3=R^4=H$; $X^-=Br^-$).

(c)

10-Methoxybenzo[b]quinolizinium bromide (4.0 g, 0.014 mol) was added to 150 mL of warm 10% potassium hexafluorophosphate in water. After stirring for 5 minutes, the precipitate which formed was collected by filtration and washed with warm water, then hexane, to afford 3.0 g (61%) of 10-methoxybenzo[b]quinolizinium hexafluorophosphate (Formula VII: $R^2=10-OCH_3$; $R^3=R^4=H$; $X^-=PF_6^-$).

(d)

To a solution of 10-methoxybenzo[b]quinolizinium hexafluorophosphate (3.0 g, 8.4 mmol) in methanol/acetonitrile (3/1, 250 mL) was added freshly distilled cyclopentadiene (25 mL). The mixture was stirred at room temperature for 2 hours, and then was allowed to stand for 16 hours. The solvent was removed in vacuo and the residue was triturated with ethyl acetate and filtered to afford 2.6 g (74%) of 10-methoxy-6,11 [3',4']cyclopentenyl-6,11-dihydrobenzo[b]quinolizinium hexafluorophosphate (Formula II $R^2=10-OCH_3$; $R^3=R^4=H$; $A=[3',4']$cyclopentenyl; $X^-=PF_6^-$).

Preparation 12

(a)

A mixture of 2-(1,3-dioxolan-2-yl)pyridine (3.9 g, 0.026 mol), 1-iodoethylbenzene (6.0 g, 0.026 mol) and acetone (50 mL) was stirred at room temperature under nitrogen. The acetone was removed, and sulfolane (50 mL) and additional 1-iodoethylbenzene (0.5 equivalents) was added and the mixture was stirred for 24 hours. The mixture was diluted with ethyl acetate, and the precipitate which formed was collected by filtration to afford 3.7 g (37%) of 1-(1-phenylethyl)-2-(1,3-dioxolan-2-yl)pyridinium iodide (Formula XI: $R^2=R^4=H$; $R^3=CH_3$; $Z^-=I^-$).

(b)

A mixture of 1-(1-phenylethyl)-2-(1,3-dioxolan-2-yl)pyridinium iodide (3.5 g, 9 mmol) and 48% hydrobromic acid (20 mL) was refluxed for 16 hours. The solvent was removed in vacuo to afford 1.9 g (76%) of 6-methylbenzo[b]quinolizinium bromide (Formula VII: $R^2=R^4=H$; $R^3=CH_3$; $X^-=Br^-$).

(c)

A mixture of 6-methylbenzo[b]quinolizinium bromide (1.8 g, 7 mmol), cyclopentadiene (2.6 g, 0.039 mol) and methanol was stirred at room temperature for 48 hours. The solvent was removed in vacuo and the residue was dissolved in water, washed with ether, treated with charcoal and filtered through celite. Sodium perchlorate (857 mg, 7 mmol) was added to the filtrate and the solution was cooled. A solid precipitated, which was collected by filtration and washed with ether to afford 365 mg (15%) of 6-methyl-6,11 [3′,4′]cyclopentenyl-6,11-dihydrobenzo[b] quinolizinium perchlorate (Formula II: $R^2=R^4=H$; $R^3=CH_3$; $A=[3′,4′]$cyclopentenyl; $X^-ClO_4^-$), as a tan solid, m p 239°-241 ° C. (dec.).

Preparation 13

A mixture of benzo[b]quinolizinium bromide (5.0 g, 0.02 mol), (Bradsher and Parham, J. Org. Chem. 1963, 28, 83-85, Example VIIa), methanol (3 mL), water (40 mL) and cyclopentene (3.5 mL, 0.04 mL) was heated to 65° C. in a sealed tube for 2 hours. Additional methanol (5.0 mL) was added and heating was continued at 65° C. for 8 hours. Additional methanol (3.0 mL) was again added and the mixture was heated at 65 ° C. for about 17 hours. The solvent was removed in vacuo and the residue was purified by column chromatography on silica eluting with ethyl acetate/PAW (1/1, wherein PAW is pyridine/acetic acid/water (55/20/25) to afford two fractions, each of which contains a single geometric isomer, as well as a third fraction which contains 4.0 g of a mixture of both isomers. Each of the isomers was individually treated with water (20 mL), followed by sodium perchlorate to afford 0.2 g (2.8%) of 6,11 [1′,2′]cyclopentyl-6,11-dihydrobenzo[b]quinolizinium perchlorate.½ hydrate (Formula II: $R^2=R^3=R^4=H$; $A=[1′, 2′]$cyclopentyl; $X^-=ClO_4^-$), as one geometric isomer, and 0.88 g (12%) of 6,11 [1′,2′]cyclopentyl-6,11-dihydrobenzo[b]quinolizinium perchlorate. ½ hydrate (Formula II: $R^2=R^3=R^4=H$; $A=[1′,2′]$cyclopentyl; $X^-=ClO_4^-$), as the other geometric isomer. The first isomer was isolated as a white solid, m.p. 198°-201° C. and the second isomer was isolated as a tan solid, m.p. 217°-222° C.

Preparation of Final Products

Example 1

(a)

A mixture of 6,11 [1′,2′]benzo-6,11-dihydrobenzeno[b]quinolizinium perchlorate (1.4 g, 3.9 mmol) (Fields et al., J. Org. Chem. 1971, 26(20), 2995-3001, Example 4a) and 0.3 g of $PtO_2$ in THF (100 mL) was hydrogenated at 50 psi (initial pressure). The theoretical $H_2$ consumption occurred within 7 hours. The mixture was filtered and the solvent was removed in vacuo. The residue was dissolved in water, basified with 6N KOH, and extracted with ethyl acetate. The combined organic layers were dried over $K_2CO_3$ and the solvent was removed in vacuo to afford 1.31 g of crude product. The residue was recrystallized from pentane to yield 0.32 g (31.4%) of 6,11 [1′,2′]cyclohexyl-1,2,3,4,5,6,11:11a-octahydrobenzo[b]quinolizine (Formula I: $R^2=R^3=R^4=H$; $A=[1′,2′]$cyclohexyl; $R^1$=free valence), as an off-white solid, m.p. 113.0°-116.0° C.

(b)

A mixture of 6,11 [1′,2′]benzeno-6,11-dihydrobenzo[b]quinolizinium perchlorate (376 mg, 1.06 mmol) and $NaBH_4$ (160 mg, 4.2 mmol) in methanol (10 mL) was stirred at room temperature for 60 minutes. After cooling to 0° C., the mixture was acidified with 2N HCl (20 mL), stirred 10 minutes, and the solvent was removed in vacuo. The residual product was basified with conc. $NH_4OH$, and extracted with ether. The combined organic layers were washed with saturated NaCl (3X) and dried over $K_2CO_3$. The solvent was removed in vacuo, and the residue was purified by preparative thin layer chromatography on silica eluting with 10% isopropanol/isopropyl acetate to afford 24 mg (9%) of 6:11 [1′,2′]benzeno-1,4,5,6,11,11a-hexahydrobenzo[b]quinolizine, m.p. 139°-140° C. and 76 mg (27%) of 6,11 [1′,2′]benzeno-1,2,3,4,5,6,11,11a-octahydrobenzo[b]quinolizine (Formula I: $R^2=R^3=R^4=H$; A=phenyl; $R^1$=free valence), as a pinkish tan solid.

Example 2

A mixture of 11-methyl-6,11 [3′,4′]cyclopentenyl-6,11-dihydrobenzo[b]quinolizinium perchlorate (1.2 g, 3.3 mmol), $PtO_2$ and methanol was hydrogenated at room temperature and 50 psi (initial pressure) for 3 hours. The mixture was filtered and the catalyst was rinsed with ethanol and water. Toluene (40 mL) was added to the solution and the solvent was removed in vacuo. The residue was dissolved in ethyl acetate and extracted with 2N HCl. The acidic solution was then washed with ethyl acetate and the aqueous layer was basified with conc. $NH_4OH$ and extracted with ether. After drying over $K_2CO_3$, the organic solvent was removed in vacuo. The crude product was purified by column chromatography on silica eluting with ethyl acetate/hexane/isopropylamine (1/1/1%). To the purified product dissolved in acetone (20 mL) was added $CH_3SO_3H$ (33 mmol) and the solvent was removed in vacuo. The residue was dissolved in ethyl acetate, the organic solution was washed with aqueous $K_2CO_3$, and dried over $K_2CO_3$. The solvent was removed in vacuo to yield 170 mg (11%) of 11-methyl-6,11 [1′,2′]cyclopentyl-1,2,3,4,5,6,11,11a-octahydrobenzo[b]quinolizine (Formula I: $R^2=R^3=H$; $R^4=CH_3$; $A=[1′,2′]$cyclopentyl; $R^1$-free valence), as a brown oil.

Example 3

(a)

A mixture of 8-methoxy-6,11 [3′,4′]cyclopentenyl-6,11-dihydrobenzo[b]quinolizinium perchlorate (1.8 g, 4.7 mmol) and 0.2 g of $PtO_2$ in methanol (75 mL) was hydrogenated until the uptake of $H_2$ ceased. The catalyst was removed by filtration and the solvent was removed in vacuo. The residue was triturated with pentane and the precipitated solid was collected by filtration. The pentane solution was concentrated in vacuo to yield 8-methoxy-6,11 [1′, 2′]cyclopentyl-1,2,3,4,5,6,11,11a -octahydrobenzo[b]quinolizine (Formula I: $R^2=8-OCH_3$; $R^3=R^4=H$; $A=[1′,2′]$cyclopentyl; $R^1$-free valence).

(b)

A solution of 8-methoxy-6,11 [1′,2′]cyclopentyl-1,2,3,4,5,6,11,11a-octahydrobenzo[b]quinolizine (0.9 g, 3.1 mmol) in 20 mL of 48% HBr was refluxed overnight. The reaction mixture was cooled (0° C.) and the solid product was isolated by filtration. The solid product was recrystallized from methanol/ether to afford 240 mg (22%) of 8-hydroxy-6,11 [1',2']cyclopentyl-1,2,3,4,5,6,11,11a-octahydrobenzo[b]quinolizine hydrobromide (Formula I: $R^2=8-OH$; $R^3=R^4=H$; $A=[1',2']$cyclopentyl; $R^1=$free valence), as a white solid, m.p. 301° C. (dec.).

Example 4

A mixture of 9-bromo-6,11 [3',4']cyclopentenyl-6,11-dihydrobenzo[b]quinolizinium bromide (6.5 g, 0.016 mol) and 0.5 g of $PtO_2$ in 200 mL of methanol was hydrogenated on a Parr hydrogenator for 4 hours. The mixture was removed from the Parr hydrogenator, the catalyst was removed by filtration and the solvent was removed in vacuo. The residue was recrystallized from methanol/ethyl acetate to yield 4.7 g (71%) of 9-bromo-6,11 [1',2']cyclopentyl-1,2,3,4,5,6,11,11a-octahydrobenzo[b]quinolizine hydrobromide (Formula I: $R^2=9-Br$; $R^3=R^4=H$; $A=[1',2']$cyclopentyl; $R^1=$free valence), as a white solid, m.p. 233°-4° C. (dec.).

Example 5

A mixture of 9-fluoro-6,11 [3',4']cyclopentenyl-6,11-dihydrobenzo [b]quinolizinium perchlorate (7.33 g, 0.0264 mol) and 0.5 g of $PtO_2$ in 200 mL of methanol was hydrogenated on a Parr hydrogenator at 50 psi for 5 hours. The mixture was removed from the Parr hydrogenator, the catalyst was removed by filtration and the solvent was removed in vacuo. The residue was dissolved in water (20 mL), basified with conc. $NH_4OH$, and extracted with methylene chloride (3X). The organic layer was dried over $MgSO_4$ and the solvent was removed in vacuo. The yellow oil thus obtained was triturated with pentane (50 mL) and the resulting solid was dissolved in acetone and refluxed with fumaric acid while stirring. The solid product was isolated by filtration, recrystallized from isopropanol, and then 2-butanone, to yield 3.75 g (39.3%) of 9-fluoro-6,11 [1',2']cyclopentyl-1,2,3,4,5,6,11,11a-octahydrobenzo[b]quinolizine fumarate (Formula I: $R^2=9-F$; $R^3=R^4=H$; $A=[1',2']$cyclopentyl; $R^1=$free valence), as a white solid, m.p. 272°-4° C.

Example 6

A mixture of 9-nitro-6,11 [3',4']cyclopentenyl-6,11-dihydrobenzo[b]quinolizinium perchlorate (5.71 g, 0.0146 mol) and 0.2 g of $PtO_2$ in ethanol (200 mL) was hydrogenated on a Parr hydrogenator for 8 hours. After adding 3N HCl to the reaction mixture, hydrogenation was continued for an additional 2 hours. The mixture was removed from the Parr hydrogenator, the catalyst was removed by filtration and the solvent was removed in vacuo. The residue was basified with $NH_4OH$, extracted with methylene chloride, and dried over $MgSO_4$. The solvent was removed in vacuo and the residue was triturated with hexane to afford a white solid. The white solid was recrystallized from acetonitrile (3X) to yield 346 mg (8.8%) of 9-amino-6,11 [1',2']cyclopentyl-1,2,3,4,5,6,11,11a-octahydrobenzo[b]quinolizine (Formula I: $R^2=9-NH_2$; $R^3=R^4=H$; $A=[1',2']$cyclopentyl; $R^1=$free valence), as a white solid, m.p.166°-7° C.

Example 7

A mixture of 6,11 [2',3']tetrahydropyranyl-6,11-dihydrobenzo[b]quinolizinium bromide (2 g, 5.8 mmol) and 75 mg of $PtO_2$ in ethanol (100 mL) was hydrogenated on a Parr hydrogenator until $H_2$ consumption ceased. The mixture was removed from the Parr hydrogenator, the catalyst was removed by filtration and the solvent was removed in vacuo. The residue was triturated with acetonitrile and the solid product was filtered and recrystallized from isopropanol to afford 0.44 g (21.7%) of 6,11 [2',3']tetrahydropyranyl-1,2,3,4,5,6,11,11a-octahydrobenzo[b]quinolizine hydrobromide (Formula I: $R^2=R^3=R^4=H$; $A=[2',3']$tetrahydropyranyl; $R^1=$free valence), as a tan powder m.p. 295°-300° C. (dec.).

Example 8

A mixture of 6,11 [2',3']tetrahydrofuranyl-6,11-dihydrobenzo[b]quinolizinium bromide (900 mg, 2.7 mmol) in water (30 mL), $PtO_2$ and 100 mL of ethanol was hydrogenated on a Parr hydrogenator until $H_2$ consumption ceased. The mixture was removed from the Parr hydrogenator, the catalyst was removed by filtration and the solvent was removed in vacuo. The solid residue was recrystallized from ethanol/ether to yield 280 mg (30%) of 6,11 [2',3']tetrahydrofuranyl-1,2,3,4,5,6,11,11a-octahydrobenzo [b]quinolizine hydrobromide (Formula I: $R^2=R^3=R^4=H$; $A=[2',3']$tetrahydrofuranyl; $R^1=$free valence), as an off white solid, m.p. 270°-3° C.

Example 9

(a)

A mixture of 6,11 [3',4']cyclopentenyl-6,11-dihydrobenzo[b]quinolizinium bromide (26 g, 0.08 mol), $PtO_2$ (200 mg), ethanol (200 mL) and water (50 mL) was hydrogenated on a Parr hydrogenator until $H_2$ consumption ceased. The mixture was removed from the Parr hydrogenator, the catalyst was removed by filtration and the solvent was removed in vacuo to yield 25 g (94%) of an off-white solid. The product was recrystallized (2X) from ethanol/methyl-t-butyl ether to afford 6,11 [1',2']cyclopentyl -1,2,3,4,5,6,11,11a-octahydrobenzo[b]quinolizine hydrobromide (Formula I: $R^2=R^3=R^4=H$; $A=[1',2']$cyclopentyl; $R^1=$free valence), as an off-white solid, m.p. 273°-5° C.

(b)

An alternative procedure was also followed in which a mixture of 6,11 [1',2']cyclopentyl-6,11-dihydrobenzo[b]quinolizinium perchlorate (3.6 g, 0.01 mol, as a mixture of geometric isomers), ethanol (40 mL) and platinium oxide (0.3 g) was hydrogenated on a Parr hydrogenator until 40 psi of $H_2$ was consumed. 6N HCl (3.0 mL) was added to the mixture and hydrogenation was continued until an additional 25 psi of $H_2$ was consumed. The catalyst was removed by filtration, and the solvent was concentrated in vacuo to about 5 mL. Ice (20 g) was added and the mixture was treated with 35% NaOH to a pH=9.5. The aqueous solution was extracted with pentane (3x), the organic layer was dried over $K_2CO_3$ and the solvent was removed in vacuo to afford 6,11 [1', 2]cyclopentyl-1,2,3,4,5,6,11,11a-octahydrobenzo[b]quinolizine (Formula I: $R^2=R^3=R^4=H$; $A=[1',240]$cyclopentyl; $R^1=$free valence), as a pale yellow oil.

Example 10

(a)

A mixture of 9-methoxy-6,11 [3',4']cyclopentenyl-6,11-dihydrobenzo [b]quinolizinium perchlorate (2 g, 5.3 mmol) and 100 mg of PtO$_2$ in 200 mL of methanol/ethanol (50:50) was hydrogenated on a Parr hydrogenator until H$_2$ consumption ceased. The reaction mixture was removed from the Parr hydrogenator, the catalyst was removed by filtration, and the solvent was removed in vacuo to yield 2.2 g of the perchlorate salt. The residue was treated with a sodium bicarbonate solution, extracted with methylene chloride, and dried over sodium carbonate. The solvent was removed in vacuo to yield 1.99 g (98%) of 9-methoxy-6,11 [1',2']cyclopentyl-1,2,3,4,5,6,11,11a-octahydrobenzo[b]quinolizine (Formula I: R$^2$=9—OCH$_3$; R$^2$=R$^4$=H; A=[1',2']cyclopentyl; R$^1$=free valence), as an oil (b)

A solution of 9-methoxy-6,11-[1',2']cyclopentyl-1,2,3,4, 5,6,11,11a-octahydrobenzo[b]quinolizine (1.9 g, 7 mmol) in 15 mL of 48% HBr was stirred at room temperature for 24 hours and was then heated at 100° C. for 24 hours. The solution was concentrated in vacuo and the residue was recrystallized from ethanol to afford 9-hydroxy-6:11 [1',2']cyclopentyl-1,2,3,4,5,6,11,11a-octahydrobenzo [b]quinolizine hydrobromide (Formula I: R$^2$=9—OH; R$^3$=R$^4$=H; A=[1',2']cyclopentyl; R$^1$=free valence), as an off-white solid, m.p. 289°–292° C.

Example 11

A mixture of 6,11 [3',4']cyclohexenyl-6,11-dihydrobenzo[b]quinolizinium bromide (4.0 g, 0.012 mol), THF (100 mL), PtO$_2$ (200 mg) and methanol (100 mL) was hydrogenated on a Parr hydrogenator at approximately 47 psi for 6 hours. Additional PtO$_2$ (200 mg) was added and the mixture was hydrogenated for an additional 5 hours. The catalyst was removed by filtration, the solvent was concentrated in vacuo and the residue was taken up in CH$_2$Cl$_2$ and washed with 1N NaOH and the brine. The solvent was removed in vacuo and the residue was purified by column chromatography on silica eluting with ethyl acetate/PAW (2/1) wherein PAW is pyridine/acetic acid/water (55/20/25)) followed by recrystallization from acetonitrile to afford 1.3 g (41%) of 6,11 [1',2']cyclohexyl -1,2,3,4,5,6,11,11a-octahydrobenzo[b]quinolizine (Formula I: R$^2$=R$^3$=R$^4$=H; A=[1',2']cyclohexyl; R$^1$=free valence), as a white powder, m.p. 113°–116° C.

Example 12

(a)

A mixture of 10-methoxy-6,11 [3',4']cyclopentenyl-6,11-dihydrobenzo[b]quinolizinium hexafluorophosphate (2 g, 4.75 mmol) and 200 mg of PtO$_2$ in 200 mL of methanol/ethanol (1:1) was hydrogenated on a Parr hydrogenator at 50 psi for 3 hours. The mixture was removed from the Parr hydrogenator, the catalyst was removed by filtration and the solvent was removed in vacuo. The residue was dissolved in methylene chloride and washed with saturated sodium bicarbonate. The organic layer was dried over potassium carbonate and the solvent was removed in vacuo to yield 1.4 g (68.8%) of 10-methoxy-6,11 [1',2']cyclopentyl-1,2,3,4,5,6, 11,11a-octahydrobenzo[b]quinolizine (Formula I: R$^2$=10—OCH$_3$; R$^3$=R$^4$=H; A=[1',2']cyclopentyl; R$^1$=free valence).

(b)

A solution of 10-methoxy-6,11 [1',2']cyclopentyl-1,2,3,4, 5, 6,11,11a-octahydrobenzo[b]quinolizine hexafluorophosphate (1.3 g,3 mmol) in 10 mL of 48% hydrogen bromide was allowed to react at 100° C. for 12 hours. The reaction mixture was concentrated in vacuo to ⅓ volume and the solid product which precipitated was isolated by filtration. The solid product was redissolved in hot ethanol (50 mL), filtered, and the filtrate was cooled and diluted with isopropyl acetate (100 mL). After cooling and filtration, there was obtained 400 mg (26.6%) of 10-hydroxy-6,11 [1',2']cyclopentyl-1,2,3,4,5,6,11,11a-octhydrobenzo[b]quinolizine hydrobromide (Formula I: R$^2$=10—OH; R$^3$=R$^4$=H; A=[1',2']cyclopentyl; R$^1$=free valence), m.p. 138° C.

Example 13

A mixture of 6-methyl-6,11 [1',2']cyclopentenyl-6,11-dihydrobenzo[b]quinolizinium perchlorate (300 mg) and 50 mg of PtO$_2$ in 100 mL of ethanol was hydrogenated on a Parr hydrogenator at 50 psi until H$_2$ consumption ceased. The reaction mixture was removed from the Parr hydrogenator, the catalyst was removed by filtration, and the solvent was removed in vacuo. The residue was basified with a 10% potassium carbonate solution, extracted with chloroform (4X), and dried over magnesium sulfate. Upon concentration of solvent in vacuo, 400 mg (31%) of crude 6-methyl -6,11 [1',2']cyclopentyl-1,2,3,4,5,6,11,11a-octahydrobenzo [b]quinolizine (Formula I: R$^2$=R$^4$=H; R$^3$=CH$_3$; A=[1',2']cyclopentyl; R$^1$=free valence) was obtained as a purple oil. The oil was dissolved in ethyl acetate/ether, treated with charcoal and filtered to afford a clear solution. The solution was treated with HCl/ethyl acetate to afford a gummy solid which was washed with ether (2X) and then dried in vacuo. The gum was dissolved in ethyl acetate, treated with 3N NaOH, washed with brine, and the aqueous layer was backwashed with ether (1X). The organic layers were combined, dried over MgSO$_4$ and concentrated in vacuo to afford 200 mg of the product as the free base. The free base was converted into the maleate salt, reconverted into the free base; purified by preparative layer chromatography on silica eluting with 30% isopropanol/isopropyl acetate, converted into the 9-anthracene carboxylic acid salt, and finally reconverted back into the free base to afford 30 mg (14%) of the product as an oil.

Example 14

6,11 [1',2']Cyclopentyl-1,2,3,4,5,6,11,11a-octahydrobenzo[b]quinolizine (0.5 g, 1.97 mmol) of Example 9(b), methanol (30 mL) and 30% hydrogen peroxide (0.11 mL, 0.99 mol) were combined at 0° C. and warmed slowly to room temperature. After 4 days, additional 30% hydrogen peroxide (0.5 equivalents) was added and stirring was continued for two more days. PtO$_2$ was added to quench any excess 30% hydrogen peroxide, the PtO$_2$ was removed by filtration and the solvent was removed in vacuo to afford 300 mg of crude product. The crude product was purified by preparative thin layer chromatography on silica eluting with ethyl acetate/PAW (1/1); wherein PAW is pyridine/acetic acid/water (55/20/25) to afford 40 mg of 6,11 [1',2']cyclopentyl-1,2,3,4,5,6,11,11a-octahydrobenzo[b]quinolizine-5-oxide (Formula I: R$^2$=R$^3$=R$^4$=H; A=[1',2']cyclopentyl; R$^1$=O−), as a brown oil.

Example 15

Gaseous methyl bromide was passed through a cooled (0° C.) solution of ethyl acetate (25 mL) containing 300 mg (1.18 mmol) of 6,11 [1',2']cyclopentyl-1,2,3,4,5,6,11,11a-octahydrobenzo[b]quinolizine until the solution was saturated and the reaction mixture was warmed to room temperature and then refluxed briefly. The precipitated solid was isolated by filtration and washed with ether to yield 60 mg (14.6%) of 5-methyl-6,11 [1',2']cyclopentyl-1,2,3,4,5,6,11,11a-octahydrobenzo[b]quinolizinium bromide (Formula I: $R^2=R^3=R^4=H$; $A=[1',2']$cyclopentyl; $R^1=CH_3$), as an orange solid, m.p. 188°–191° C. (dec.).

BIOLOGICAL TEST RESULTS

Representative examples of the compounds of the invention have been found to possess valuable pharmacological properties. In particular, they have been found to bind to the PCP receptor and are thus non-competitive blockers (antagonists) of the effects which excitatory amino acids, such as glutamate, have upon the NMDA receptor. The compounds of the invention are thus useful in the treatment or prevention of neurodegenerative disorders such as Huntington's disease, Alzheimer's disease, amyotrophic lateral sclerosis, Down's Syndrome, senile dementia, glutaric acidaemia type I, multi-infarct dementia, Parkinson's disease, viral encephalopathies (which include, but are not limited thereto, dementia associated with HIV infections) and neuronal damage associated with uncontrolled seizures, as well as in the treatment or prevention of neurotoxic injuries associated with ischemic, hypoxic; or hypoglycemic conditions. Representative examples of such ischemic, hypoxic, or hypoglycemic conditions include strokes or cerebrovascular accidents, carbon monoxide poisoning, hyperinsulinemia, cardiac arrest, drownings, suffocation, spinal or head trauma, neonatal anoxic trauma, coronary artery bypass graft, and perinatal asphyxia.

The compounds of the invention are particularly useful in the treatment or prevention of neurotoxic injuries associated with ischemic, hypoxic; or hypoglycemic conditions, and especially ischemic, hypoxic, or hypoglycemic conditions which are associated with stroke.

The pharmacological properties of representative examples of the compounds of the invention was demonstrated by conventional in vitro biological test procedures such as the following:

[$^3$H]TCP Radioreceptor Assay (internal screen)

[$^3$H]TCP binding to PCP recognition sites was performed as described by Vignon et al. Brain Research 1983, 280, 194–197. Male Spmgue-Dawley rats were sacrificed by decapitation, and whole brains were homogenized in 10 volumes (wt/vol) of cold Tris-HCl buffer (50 mM, pH 7.7) using a Brinkmann Polytron (setting 6, 30 sec). The homogenate was centrifuged at 40,000×g for 10 min at 4° C. The supernatant was decanted, and the homogenization and centrifugation steps were repeated twice as described above. Following this, the pellet was resuspended in Tris-HCl (5 mM, pH 7.7) at a tissue concentration of 0.5–0.75 g/ml, and one ml aliquots were frozen at −70° C. unto use. The binding characteristics for PCP recognition sites were not altered by the freezing of membrane suspensions.

On the day of the assay, membrane aliquots were thawed, resuspended in fresh 5 mM Tris-HCl buffer at a tissue concentration of 1 mg/ml, and stored on ice until use. Each assay tube contained 100 μl of [$^3$H]TCP at a final concentration of approximately 1 nM, 100 μl of various concentrations of the compounds of interest, 500 μl of the tissue suspension and 300 μ of buffer to a final assay volume of 1 ml and a final protein concentration of 0.5 mg/tube. Non-specific binding was defined by addition of a final concentration of 100 μM PCP to blank tubes. All tubes were incubated at room temperature for 25 min before termination of the reaction by rapid filtration over Whatman GF/B glass fiber filters that had been presoaked in a solution of 0.5% polyethyleneimine for at least 1 hr prior to use. Filters were washed with three 4 ml volumes of cold Tris buffer. Following addition of scintillation cocktail, the amount of bound radioactivity was determined by liquid scintillation spectrometry using a Beckman LS 5000 TA liquid scintillation counter with an efficiency for tritium of approximately 55%. Inhibition constants ($K_i$ values) were calculated using the EBDA/LIGAND program (McPherson, J. Pharmacol. Meth. 1985, 14, 213–228), purchased from Elsevier/Biosoft, Inc. Results are reported as $K_i$ values which are expressed as the mean of at least two separate determinations.

Representative compounds of the invention were also tested in an external [$^3$H]TCP radioreceptor assay using the following protocol:

[$^3$H]TCP Radioreceptor Assay (external screen)

A procedure similar to that described above for the [$^3$H]TCP radioreceptor assay (internal screen) was utilized except that the whole rat forebrain membranes were incubated at 25° C. for 60 minutes rather than at room temperature for 25 minutes, before termination of the reaction. The results are reported as a percent (%) inhibition of binding at 10 μM.

Antagonism of NMDA-induced Neurotoxicity in Cultured Neurons

Preparation of cultured cortical neurons

Pregnant, Swiss-Webster mice were obtained from Taconic 0 Farms (Germantown, N.Y.) and sacrificed 16 days post conception. Fetuses were removed and placed in a sterile dish containing Hank's balanced salt solution (HBSS), pH 7.4. Brain cortices were dissected, meninges were removed, the tissue was minced and placed into a solution of HBSS containing 0.25% (w/v) trypsin at 37° C. for 15 minutes. Tissue was then triturated with a sterile pasteur pipet, diluted with minimal essential media (Gibco 330–1430), pH 7.4, supplemented with 10% horse serum, 10% fetal calf serum, 2 mM l-glutamine, 21 mM d-glucose, 2.2 g/L sodium bicarbonate, 1000 U/ml penicillin, and 1,000 μg/ml streptomycin. Cells were plated onto Falcon primaria 96 well plates at a final density of 50,000 cells/well and incubated at 37° C. in the presence of 5% (v/v) carbon dioxide. After 5 days, plating media was replaced with maintenance media containing minimal essential media (Gibco 330–1430), pH 7.4, supplemented with 10% horse serum, 10% l-glutamine, 21 mM d-glucose, 2.2 g/l sodium bicarbonate, 1,000 U/ml penicillin, 1,000 μg/ml streptomycin, and 10 μM cytosine arabinoside. On days 7 and 10, media was replaced with maintenance media as above lacking the cytosine arabinoside. Experiments were conducted on day 13.

Neuroprotection Assessment

Day 13 cultured cortical neurons were washed twice with minimal essential media, pH 7.4 and then exposed for 30 minutes to 500 μM N-methyl-D-aspartic acid (NMDA) with or without varying concentrations of test agents. Dizocilpine (MK-801) at a final concentration of 10 μM MK-801 was routinely included as a positive control. MK-801 and test agents were prepared in minimal essential media supplemented with 21 mM d-glucose and 2.2 g/L sodium bicarbonate (MEM). After 30 minutes, media was replaced with MEM alone. Exposure of neurons to test agents was limited to the NMDA treatment period. Twenty-four hours after removal of NMDA, an aliquot of media from each well was removed for assessment of cell injury by determining lactate dehydrogenase (LDH) activity by the method of Wroblewski and LaDue Proc. Sec. Exp. Biol. Med. 1955, 90, 210–213. The results are expressed as an $IC_{50}$ (in nM) value (concentration causing 50% inhibition) for the antagonism of NMDA—induced neurotoxicity.

Table 1 summarizes the results obtained from the testing of representative compounds of the invention in the [$^3$H]TCP radioreceptor assay (internal screen and external screen) as well as in the antagonism of NMDA-induced neurotoxicity in cultured neurons.

TABLE 1

| Example Number | [$^3$H]TCP (internal screen) $K_i$(nM) | [$^3$H]TCP (external screen) Percent inhibition (%) @10 μM | Antagonism of NMDA-induced neurotoxicity ($IC_{50}$ in nM) |
|---|---|---|---|
| 1a | 134 | — | — |
| 1b | 333 | — | — |
| 2 | 40 | — | — |
| 3b | 27.9 | — | — |
| 4 | 43.7 | — | — |
| 5 | 20 | — | — |
| 6 | 11.8 | — | — |
| 7 | 1416 | — | — |
| 8 | 606 | — | 12200 |
| 9a | 15.4 | 100 | 100 |
| 10b | 2.31 | — | 42 |
| 11 | 219 | — | — |
| 12b | 2.29 | — | — |
| 13 | 8.87 | — | — |
| 14 | 33.1 | — | — |
| 15 | 22.3 | — | — |

The compounds of the invention can be prepared for pharmaceutical use by conventional pharmaceutical procedures that are well known in the art; that is, by formulating a pharmaceutical composition which comprises compounds of the invention or their pharmaceutically acceptable salts together with one or more physiologically acceptable carriers, adjuvants, diluents or vehicles, for oral administration in solid or liquid form, parenteral administration, topical administration or aerosol inhalation administration, and the like.

Solid compositions for oral administration include compressed tablets, pills, powders and granules. In such solid compositions, the active compound is admixed with at least one inert diluent such as starch, calcium carbonate, sucrose or lactose. These compositions may also contain additional substances other than inert diluents, e.g., lubricating agents, such as magnesium stearate, talc and the like.

Liquid compositions for oral administration include pharmaceutically acceptable emulsions, solutions, suspensions, syrups and elixirs containing inert diluents commonly used in the art, such as water and liquid paraffin. Besides inert diluents such compositions may also contain adjuvants, such as wetting and suspending agents, and sweetening, flavoring, perfuming and preserving agents. According to the invention, the compounds for oral administration also include capsules of absorbable material, such as gelatin, containing said active component with or without the addition of diluents or excipients.

Preparations according to the invention for parenteral administration include sterile aqueous, aqueous-organic, and organic solutions, suspensions and emulsions. Examples of organic solvents or suspending media are propylene glycol, polyethylene glycol, vegetable oils such as olive oil and injectable organic esters such as ethyl oleate. These compositions can also contain adjuvants such as stabilizing, preserving, wetting, emulsifying and dispersing agents.

Preparations according to the invention for topical administration or aerosol inhalation administration include dissolving or suspending a compound of the invention in a pharmaceutically acceptable vehicle such as water, aqueous alcohol, glycol, oil solution or oil-water emulsion, and the like.

If desired, the compounds of the invention can further be incorporated into slow release or targeted delivery systems such as polymer matrices, liposomes, and microspheres.

The percentage of active component in such compositions may be varied so that a suitable dosage is obtained. The dosage administered to a particular patient is variable depending upon the clinician's judgment using as criteria: The route of administration, the duration of treatment, the size and physical condition of the patient, the potency of the active component and the patient's response thereto. An effective dosage amount of the active component can thus readily be determined by the clinician after a consideration of all criteria and using his best judgment on the patient's behalf.

We claim:

1. A compound of the formula:

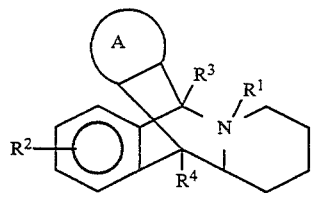

wherein:

$R^1$ is lower-alkyl, $O^-$, or a free valence;

$R^2$ is hydrogen, or one substituent in any of the 7-, 8-, 9-, or 10-positions selected from the group consisting of amino, halogen, hydroxy, and lower-alkoxy;

$R^3$ is hydrogen, or lower-alkyl;

$R^4$ is hydrogen, or lower-alkyl; and

A is a cycloalkyl ring, or a saturated monocyclic 5- or 6-membered heterocyclic ring containing a single oxygen atom; or a pharmaceutically acceptable acid-addition salt of basic members thereof; or when $R^1$ is lower-alkyl a quaternary ammonium salt thereof.

2. A compound according to claim 1 wherein $R^2$ is hydrogen, or one substituent in any of the 8-, 9-, or 10-positions selected from the group consisting of amino, halogen and hydroxy.

3. A compound according to claim 2 wherein A is a cycloalkyl, [2',3']tetrahydrofuranyl, or [2',3']-tetrahydropyranyl ring.

4. A compound according to claim 3 wherein $R^3$ is hydrogen, or methyl; and $R^4$ is hydrogen or methyl.

5. A compound according to claim 4 wherein $R^1$ is methyl, $O^-$, or a free valence; and $R^2$ is hydrogen, or one substituent in any of the 8-, 9-, or 10-positions selected from the group consisting of amino, bromine, fluorine and hydroxy.

6. A compound according to claim 5 wherein A is a cyclopentyl, cyclohexyl, [2',3']tetrahydrofuranyl, or [2',3']-tetrahydropyranyl ring.

7. 9-Hydroxy-6,11 [1',2']cyclopentyl-1,2,3,4,5,6,11,11a-octahydrobenzo[b]quinolizine or an acid-addition salt thereof according to claim 6.

8. 10-Hydroxy-6,11 [1',2']cyclopentyl-1,2,3,4,5,6,11,11a-octahydrobenzo [b]quinolizine or an acid-addition salt thereof according to claim 6.

9. A pharmaceutical composition which comprises a compound of the formula:

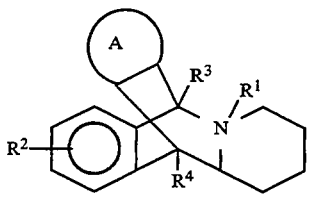

wherein:
$R^1$ is lower-alkyl, $O^-$, or a free valence;
$R^2$ is hydrogen, or one substituent in any of the 7-, 8-, 9-, or 10-positions selected from the group consisting of amino, halogen, hydroxy, and lower-alkoxy;
$R^3$ is hydrogen, or lower-alkyl;
$R^4$ is hydrogen, or lower-alkyl;
A is a cycloalkyl ring, a phenyl ring, or a saturated monocyclic 5-or 6-membered heterocyclic ring containing a single oxygen heteroatom; or a pharmaceutically acceptable acid-addition salt of basic members thereof; or when $R^1$ is lower-alkyl a quaternary ammonium salt thereof; together with a pharmaceutically acceptable carrier, adjuvant, diluent, or vehicle.

10. A pharmaceutical composition according to claim 9 wherein A is a cycloalkyl ring, or a saturated monocyclic 5-or 6-membered heterocyclic ring containing a single oxygen heteroatom.

11. A pharmaceutical composition according to claim 10 wherein $R^2$ is hydrogen, or one substituent in any of the 8-, 9-, or 10-positions selected from the group consisting of amino, halogen and hydroxy; and A is a cycloalkyl, [2',3']tetrahydrofuranyl, or [2',3']tetrahydropyranyl ring.

12. A pharmaceutical composition according to claim 11 wherein:
$R^1$ is methyl, $O^-$, or a free valence;
$R^2$ is hydrogen, or one substituent in any of the 8-, 9-, or 10-positions selected from the group consisting of amino, bromine, fluorine and hydroxy;
$R^3$ is hydrogen, or methyl; and
$R^4$ is hydrogen, or methyl.

13. A pharmaceutical composition according to claim 12 wherein A is a cyclopentyl, cyclohexyl, [2',3']tetrahydrofuranyl, or [2',3']tetrahydropyranyl ring.

14. A pharmaceutical composition according to claim 13 wherein the compound is 9-hydroxy-6,11 [1',2']cyclopentyl-1,2,3,4,5,6,11,11a-octahydrobeno[b]quinolizine, or 10-hydroxy-6,11 [1',2']cyclopentyl-1,2,3,4,5,6,11,11a-octahydrobenzo[b]quinolizine; or an acid-addition thereof.

15. A method for the treatment of neurodegenerative disorders, or neurotoxic injuries which comprises administering to a patient in need of such treatment an effective amount of a compound of the formula:

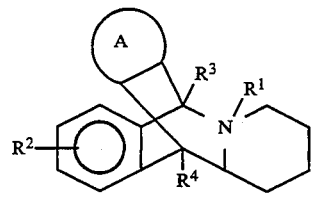

wherein:
$R^1$ is lower-alkyl, $O^-$, or a free valence;
$R^2$ is hydrogen, or one substituent in any of the 7-, 8-, 9-, or 10-positions selected from the group consisting of amino, halogen, hydroxy, and lower-alkoxy;
$R^3$ is hydrogen, or lower-alkyl;
$R^4$ is hydrogen, or lower-alkyl;
A is a cycloalkyl ring, a phenyl ring, or a saturated monocyclic 5-or 6-membered heterocyclic ring containing a single oxygen heteroatom; or a pharmaceutically acceptable acid-addition salt of basic members thereof; or when $R^1$ is lower-alkyl a quaternary ammonium salt thereof.

16. A method according to claim 15 wherein A is a cycloalkyl ring, or a saturated monocyclic 5-or 6-membered heterocyclic ring containing a single oxygen heteroatom.

17. A method according to claim 16 wherein $R^2$ is hydrogen, or one substituent in any of the 8-, 9-, or 10-positions selected from the group consisting of amine, halogen and hydroxy; and A is a cycloalkyl, [2',3']tetrahydrofuranyl, or [2',3']tetrahydropyranyl ring.

18. A method according to claim 17 wherein; $R^1$ is methyl, $O^-$, or a free valence; $R^2$ is hydrogen, or one substituent in any of the 8-, 9-, or 10-positions selected from the group consisting of amine, bromine, fluorine and hydroxy; $R^3$ is hydrogen, or methyl; and $R^4$ is hydrogen, or methyl.

19. A method according to claim 18 wherein A is a cyclopentyl, cyclohexyl, [2',3']tetrahydrofuranyl, or [2',3']-tetrahydropyranyl ring.

20. A method according to claim 19 wherein the compound is 9-hydroxy-6,11 [1',2']cyclopentyl-1,2,3,4,5,6,11,11a-octahydrobenzo[b]quinolizine, or 10-hydroxy-6,11 [1',2']cyclopentyl-1,2,3,4, 5,6,11,11a-octahydrobenzo[b]quinolizine; or an acid-addition salt thereof.

21. A method according to claim 15 for the treatment of neurodegenerative disorders.

22. A method according to claim 15 for the treatment or prevention of neurotoxic injuries.

23. A method according to claim 22 wherein said neurotoxic injuries are associated with ischemic, hypoxic, or hypoglycemic conditions.

24. A method according to claim 23 wherein said ischemic, hypoxic, or hypoglycemic conditions are associated with stroke.

* * * * *